Aug. 1, 1972 R. S. MOORE Plant Pat. 3,245
MINIATURE ROSE PLANT
Filed Jan. 11, 1971
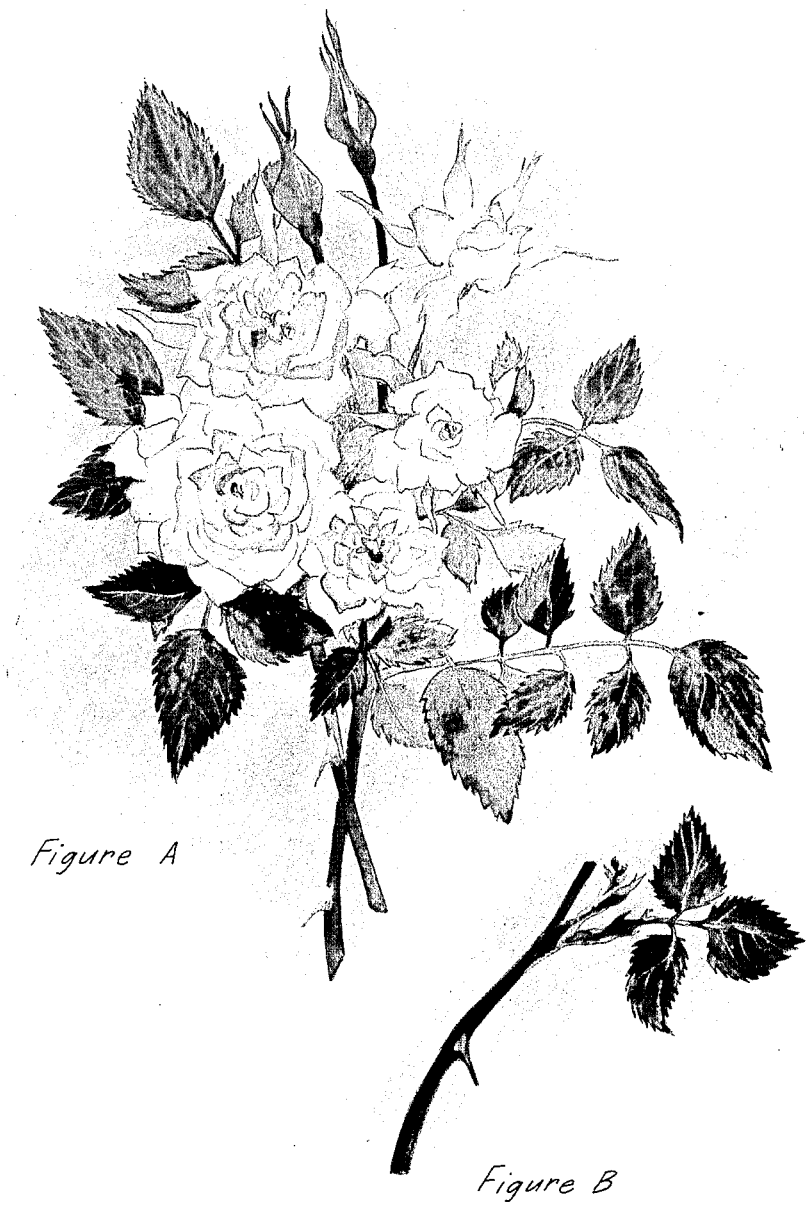
Figure A
Figure B
WITNESS
Jeanette Nunn Copley
INVENTOR
Ralph S. Moore

United States Patent Office

Plant Pat. 3,245

Patented Aug. 1, 1972

3,245

MINIATURE ROSE PLANT

Ralph S. Moore, 2519 E. Noble Ave.,
Visalia, Calif. 93277

Filed Jan. 11, 1971, Ser. No. 105,747

Int. Cl. A01h 5/00

U.S. Cl. Plt.—7 1 Claim

The present invention relates to a new and distinct variety of hardy, dwarf, bush type rose plant of the miniature class; the variety being primarily characterized—as to novelty—by buds and flowers having a color blend of white and pink of varying intensity (or degree) which in general color effect is pink.

The variety is futher characterized by:

An abundance of bloom, with flowers borne singly or several to the stem in loose clusters or sprays.

Little or no fragrance.

A plant which is vigorous, of rounded spreading shape and with semi-glossy, moderately small foliage with pointed leaflets; the flowers and foaliage being similar in size to the variety "Yellow Doll" (United States Plant Pat. No. 2450). The plant, which has a normal height of 12 to 14 inches can easily be maintained at 10 inches or less by occasional trimming.

A plant which grows and blooms satisfactoritly both in greenhouse and outdoors; is a good for growing in pots; and provides excellent garden decoration as well as cut flowers.

The present variety of miniature rose was originated by me at my nursery located at Visalia, California, under conditions of careful control and observation, as a cross between "Little Darling" (Floribunda—Plant Pat. No. 1581, expired) as the seed parent and an unnamed variety [(Rose Wichuraiana X Floradora) X (Oakington Ruby X Floradora)] all unpatented kinds, as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the Britich Colour Council Horticultural Colour Chart, except where common terms of color definition are employed.

Type: Hardy; dwarf; bush; seedling; greenhouse; outdoors; cut ffowers; garden decoration; potted plant.

Class: Miniature.

Flowers: Continuity continuous; repeat bloom all season.

Fragrance: Little or none.

Flowers borne: Singly and several together (3 to 5) on strong, medium length stems.

Quantity of bloom: Abundant both outside and in greenhouse.

Bud:

*Peduncle.*—Medium length; slender but sturdy; erect; medium green, sometimes tinted bronze; with numerous very small short hairs. Before calyx breaks; Size—small. Form medium long; pointed; with foliaceous appendages and numerous tiny short hairs on surface of bud; with foliaceous parts extending beyond the tip of the bud equal to one half or more of its length. Color—medium green, often tinted with bronze. As calyx breaks, color—near white to soft pink (changing to a deeper pink in cooler weather) often showing soft yellow tones near base of petal; Size—small.

Bloom:

*Size when fully open.*—Small, averaging about 1½ inch.

*Petalage.*—Very double—70 to 80 (plus several narrow petaloids) arranged regularly.

*Form.*—Slightly cupped at first, becoming more flat in the center, with petals rolled loosely outward, and later at maturity rounded with higher center with petals rolled loosely outward and downward.

Petals: Fairly thick; satiny both inside and outside.

*Shape.*—Outside petals, broad lanceolate (almost round with wedge shaped base and acute tip); Intermediate—broad lanceolate with acuate tip; Inside—lanceolate with actute tip.

Color: Newly opened flower from a plant grown outdoors October 1970; Visalia, California.

*Outside petal.*—Outside surface—white or near white, overlaid near tip with Magenta 27/2 and gradually blending to white in the lower one half or more of petal; Inside surface—white or near white overlaid near tip with Magenta 27, Magenta 27/1 or lighter shade and blending (mottled) into white on upper one half of petal.

*Intermediate petal.*—Outside surface—white or near white with some color from inside surface bleeding through on upper ⅓ of petal surface; Inside surface—white or near white overlaid with Magenta 27 and blending (mottled) into white on lower one half or more of petal.

*Inner petal.*—Outside surface—white or near white with color from inside surface bleeding through near tip portion of petal; inside surface—essentially same as intermediate petal.

*General color effect newly opened flowers.*—Soft pink color, usually aging deeper. Three days open—soft to medium pink (slightly lavenderish or magneta)

*Behavior.*—As flowers age petals usually become darker shade (often quite red in cool weather of spring and fall) before dropping off. Spent petals drop off (may hang on in cool damp weather.)

*Flower longevity (October 1970)*—bush in garden or pot 4 to 5 days or longer. Cut flowers at living room temperature, 3 to 4 days.

*Reproductive organs*

Stamens: Few, arranged irregularly about pistil; sometimes mixed with petaloids.

Filaments: Medium; yellow.

Pollen: Small amount; yellow.

Pistils: Average number.

Styles: Uneven; medium to short; bunched.

Stigma: Nearly white or pale yellow.

Ovaries: All enclosed in calyx.

Hips: Few or none.

Sepals: Permanent; spear shaped; recurved (fold back against peduncle).

Seeds: Few or none.

Foliage:

*Leaves.*—Compound of five leaflets, sometimes seven; abundant; small to moderately small; leathery; semiglossy.

*Leaflets.*—Shape—Broad lanceolate; apex acute; base acute or rounded acute. Margin serrate. Color—Normal green; new growth sometimes lightly tinted bronze. Rachis.—Medium strength; upper side smooth except for few very tiny prickles, grooved; under side sparsely thorny with few or no prickles. Stipules—Fairly long;

medium width; medium length narrow points which turn out at about 45 degrees.

Growth:

*Habit.*—Dwarf; bushy; rounded; much branched.

*Growth.*—Free; vigorous.

*Canes.*—Medium; slender.

*Main steams.*—Color—dull green. Thorns—few, medium length; hooked (curved) slightly downward; color—brown. Prickles—none. Hairs—none.

*Branches.*—Color—medium green. Thorns—sparsley thorney; medium length; hooked (curved), downward. Medium to short oval base; color—brown. Prickles—none. Hairs—none.

*New shoots.*—Color—medium green, often tinted bronze. Thorns—few to moderate; medium length; curved downward. Reddish to brown color; sharp points; base oval. Prickles—none. Hairs—none.

The miniature rose plant and its flowers as herein described may vary in slight detail due to climatic, soil and cultural conditions under which the variety may be grown; the present description being of the variety as grown at Visalia, California.

The following is claimed:

1. A new and distinct variety of miniature rose plant of hardy, dwarf, rounded, much branched, bush type, as illustrated and described, characterized by buds and flowers resembling the "Yelow Doll" (Plant Patent No. 2450) miniature rose in general form and size, the color being a blend of pink and white of varying degree, the petals having more pink on the top side and more white on the reverse; the general color effect being pink; and further characterized by a plant which is of vigorous and compact growth, easy to propagate from cuttings, with small leathery, semi-glossy foliage; and abundance of bloom, with flowers borne singly or several to stem in loose clusters or sprays.

No reference cited.

ROBERT E. BAGWILL, Primary Examiner